US006887678B2

(12) United States Patent
Bristow

(10) Patent No.: US 6,887,678 B2
(45) Date of Patent: May 3, 2005

(54) METHOD FOR THE QUANTITATIVE DETERMINATION OF PROTEINASE INHIBITORS

(76) Inventor: Cindy L. Bristow, 410 E. 78th St., Apt. 1B, New York, NY (US) 10021

( * ) Notice: Subject to any disclaimer, the term of this patent is extended or adjusted under 35 U.S.C. 154(b) by 269 days.

(21) Appl. No.: 10/105,719

(22) Filed: Mar. 25, 2002

(65) Prior Publication Data

US 2002/0146756 A1 Oct. 10, 2002

Related U.S. Application Data

(63) Continuation-in-part of application No. 09/452,699, filed on Dec. 2, 1999, now abandoned.
(60) Provisional application No. 60/110,580, filed on Dec. 2, 1998.

(51) Int. Cl.[7] ................................................. C12Q 1/37
(52) U.S. Cl. ......................... 435/23; 435/69.2; 435/184
(58) Field of Search ............................ 435/23, 4, 69.2, 435/184

(56) References Cited

U.S. PATENT DOCUMENTS 4,493,891 A * 1/1985 Travis ......................... 435/23
4,697,003 A * 9/1987 Coan .......................... 530/380
5,073,487 A * 12/1991 Lloyd .......................... 435/23
5,773,430 A * 6/1998 Simon et al. ................ 514/152
6,093,804 A * 7/2000 Ralston et al. .............. 530/416

FOREIGN PATENT DOCUMENTS

| DE | 39 38 971 A1 | * | 5/1991 | |
| EP | 0 288 841 A2 | * | 11/1998 | |
| RU | 2039983 C1 | * | 7/1995 | G01N/33/48 |
| SU | 1573430 A | * | 6/1990 | G01N/33/68 |

OTHER PUBLICATIONS

Bristow, C. Self Antigen Prognostic for Human Immunodeficiency Virus Disease Progression. Clinical and Diagnostic Lab Immunology. 8(5)937–942, Sep. 2001.*

* cited by examiner

Primary Examiner—Ralph Gitomer
(74) Attorney, Agent, or Firm—William R. Moran

(57) ABSTRACT

A method is provided for the quantitative determinations of active and inactive concentrations of proteinase inhibitors, such as $\alpha_1 PI$ and $\alpha_2 M$, in the body fluids of humans and animals.

10 Claims, 5 Drawing Sheets

METHOD FOR THE QUANTITATIVE DETERMINATION OF PROTEINASE INHIBITORS

RELATED APPLICATIONS

This application is a continuation-in-part of U.S. patent application, Ser. No. 09/452,699, filed Dec. 2, 1999, now abandoned, which in turn claims priority under provisional application 60/110,580, filed Dec. 2, 1998, the entire contents of both applications being incorporated herein by reference.

BACKGROUND OF THE INVENTION

1) Field of the Invention

This invention relates to a method for the quantitative determination of the specific activity of proteinase inhibitors. In one aspect, the invention is directed to the quantitative determination of inactive $\alpha_1$ Proteinase Inhibitor in bodily fluids such as human serum or plasma.

2) Background Art

Emerging evidence suggests a functional link between proteinases and cell signaling. As would be predicted, activation and inactivation of proteinase-activated receptors are selective, e.g., the thrombin-activated receptor can be inactivated by cathepsin G or neutrophil elastase. Examination of the influence of proteinase inhibitors on proteinase-activated receptors is complicated by the variance in affinities, concentrations, and species of proteinase inhibitors represented in serum. The proteinase inhibitor in serum exhibiting the greatest concentration is $\alpha_1$ proteinase inhibitor ($\alpha_1$PI, $\alpha_1$-antitrypsin), and the proteinase inhibitor encompassing the broadest spectrum is $\alpha_2$ macroglobulin ($\alpha_2$M).

In the acute phase of inflammation, quantitative levels of $\alpha_1$PI have been reported to significantly increase, as do proteolytic fragmentation and proteinase complexation, both of which can diminish the functional capacity of $\alpha_1$PI. The functional capacity of $\alpha_1$PI during the acute phase has not previously been examined. Further, in some situations, the association of $\alpha_2$M with neutrophil elastase in plasma is competitively favored, and in this case elastase-mediated proteolysis of low-molecular-weight peptides and cytokines can persist. The relative concentrations of elastolytic proteinases, the inhibitor $\alpha_1$PI, and the substrate-restricting $\alpha_2$M form a tightly regulated mechanism for discreet targeting of elastase activity.

It has been previously observed using serially diluted serum that the residual uninhibited enzymatic activity of exogenously added elastase exhibits bimodal regulation. The bimodal behavior of serum was demonstrated to result from the dual activities of $\alpha_1$PI and $\alpha_2$M; however, these investigators did not attempt to derive a numerical value for quantitating the active fraction of $\alpha_1$PI. While elastase is completely inhibited by $\alpha_1$PI, association of elastase with $\alpha_2$M excludes its activity except toward low molecular substrates. When the concentration of $\alpha_2$M exceeds that of elastase, catalytic activity if unaffected by adding $\alpha_1$PI since $\alpha_2$M is not replaced by $\alpha_1$PI in these complexes. When the concentration of elastase exceeds that of $\alpha_2$M in this scenario, elastase is available for complexing with added $\alpha_1$PI resulting in a decrease in catalytic activity. Physiologic concentrations of the common phenotypes of $\alpha_1$PI have been approximated as 20–53 $\mu$M and that of $\alpha_2$M as 1.56–4.96 $\mu$M so that as serum is diluted and incubated with a constant concentration of elastase, the contribution from $\alpha_2$M in elastase protection becomes negligible by this method of detection, and the contribution from $\alpha_1$PI is detected as increased inhibition. On the other hand, as serum becomes excessively dilute, the contribution from $\alpha_1$ PI also becomes negligible to detection resulting in decreased inhibition. Therefore, a serum dilution exists at which minimum catalytic activity can be measured by exploiting the properties of unequal serum concentration and unequal outcomes of complexes between elastase and $\alpha_1$PI and $\alpha_2$M. The maximum reduction in catalytic activity is a measure of the functionally active concentration of $\alpha_1$PI in competition with $\alpha_2$M for elastolytic enzymes. The relationship between reduction in catalytic activity and the precise quantitation of functional $\alpha_1$PI in competition with $\alpha_2$M has not previously been examined.

Proteinase inhibition is only one of the diverse biologic activities of $\alpha_1$PI and $\alpha_2$M including alteration of the cellular effects of polymorphonuclear neutrophils, found that $\alpha_1$PI It decreases antigen-driven, PHA and, Con A, but not PWM, lymphocyte responsiveness. In fact, inhibition of DNA synthesis and proliferation by $\alpha_1$PI has been demonstrated in erythroid progenitor cells and lymphocytes. It has been reported that $\alpha_1$PI deficient serum mediates enhancement of lymphocyte response to PHA and increases zymosan activation of monouclear cells and PMN. The ability to measure the functional capacity of proteinase inhibitors in serum is paramount to determining the interrelationship between proteinase inhibitors and immune responsiveness in pathology. Association rates previously derived using isolated proteinases and inhibitors suggested the feasibility for measuring these activities in serum.

Quantitative determination of serum $\alpha_1$PI has traditionally been performed nephelometrically; however, antigenically quantitated levels may not be representative of functional capacity. It has previously been observed that $\alpha_1$PI in serum exhibits bimodal behavior as the result of various concentrations of proteinase inhibitors, specifically $\alpha_2$macro-globulin ($\alpha_2$M) and inter-a-trypsin inhibitor, which compete in binding to a panel of serine proteinases. Consequently, it has not previously been possible to assign a numerical value for the specific activity of these competing proteinase inhibitors in serum.

In J. Clin. Chem. Clin. Biochem, Vol. 25, 1987, pp. 167–172, M. C. Gaillard, et al disclosed the determination of functional activity of $\alpha_1$ proteinase inhibitors and $\alpha_2$ macroglobulin in human plasma using elastase. They were able to devise an assay method to determine the amounts of functional activity of $\alpha_1$ proteinase inhibitors and $\alpha_2$ macroglobulin respectively in human plasma.

The method of Gaillard, et al employed mixing elastase with $\alpha_1$, proteinase inhibitor and $\alpha_2$ macroglobulin, all three with some degree of purity, but with undetermined activity. Their method gives a result, the equivalence point ($V_e$) used in calculating "total elastase inhibiting capacity which is defined as the number of ml of plasma required to bind 1 $\mu$mol of porcine pancreatic elastase." While this is an important finding, however, the value for total elastase binding activity is not reproducible using varying sources or concentrations of elastase as demonstrated in Bristow et 1998, Clin. Immunol. Immunopathol. Nor does the method of Gaillard, et al give any information about whether $\alpha_1$ proteinase inhibitor is being degraded or is at steady state. Degradation occurs during inflammation, and it is desirable to detect degradation of $\alpha_1$ proteinase as a prognostic indication of disease state. For this reason, the present invention sought to determine the relationship between the equivalence point described by Gaillard, et al and the number of total molecules, active molecules, and inactive molecules of $\alpha_1$ proteinase inhibitor in serum and other complex body fluids. The experimental method to define this relationship was to observe the change in residual catalytic activity of elastase when a quantifiable number of functioning molecules of elastase were incubated with a quantifiable number of functioning molecules Of $\alpha_2$ macroglobulin before or at the same time as addition of a quantifiable number of functioning molecules of $\alpha_1$ proteinase inhibitor. By varying the three numbers of molecules, it was possible to derive the theoretical relationship between elastase inhibiting capacity and the ratio of elastase bond to $\alpha_1$ proteinase inhibitor or $\alpha_2$ macroglobulin. Detivation of the theoretical relationship between elastase bound to $\alpha_1$ proteinase inhibitor or $\alpha_2$ macroglobulin in competition (herein referred to as the first unique derivation) is unique to the instant method and has not been attempted previously.

However, derivation of a theoretical relationship does not necessarily imply a physiological relationship. Therefore, the theoretical relationship was tested using serum from healthy individuals with known steady state levels of antigenically determined $\alpha_1$ proteinase inhibitor. Application of the first unique derivation to the quantification of serum elastase inhibiting activity allowed the second unique step of the instant method (herein referred to as the second unique derivation), the relationship between the "equivalence point" ($V_e$ in units of plasma volume), the number of elastase molecules added to serum, and residual catalytic activity (in units of elastase molecules).

However, derivation of the relationship between elastase molecules added to serum and residual catalytic activity still does not yield the number of molecules of $\alpha_1$ proteinase inhibitor or $\alpha_2$ macroglobulin in serum. Application of the second unique derivation to sera from a sufficiently large population of individuals allowed the third unique step of the instant method (herein referred to as the third unique derivation), the relationship between residual catalytic activity and the number of functionally active molecules of $\alpha_1$ proteinase inhibitor or $\alpha_2$ macroglobulin.

Of considerable significance, these three unique derivations allow for the first time, detection of degraded or inactive $\alpha_1$ proteinase inhibitor as a prognostic indication of disease state. Prior to the present invention, there has never existed art to measure inactive proteinase inhibitors in complex body fluids.

During inflammation, the total concentration of serum $\alpha_1$ PI proteinase inhibitor increases two-to-four fold. However, the "total elastase inhibiting activity" as determined by the method of Gaillard, et al may or may not remain at steady state. Using the instant method, recently published evidence (Bristow, et al, 2001. Clin. Diagn. Lab. Immnunol. 8: p. 938) discloses that inactive $\alpha_1$ proteinase inhibitor is strongly correlated with HIV disease progression ($p<3\times10^{-8}$). Importantly, in AIDS, the total and active concentrations of $\alpha_1$ proteinase inhibitor were not statistically different from normal, but inactive $\alpha_1$ proteinase inhibitor was significantly elevated ($p<0.0001$). These data are compelling that detecting inactive al proteinase inhibitor using the instant method provides a prognostic indicator in disease progression for which there is no prior art.

By applying known constants representing the association of proteinase inhibitors with porcine pancreatic elastase (PPE), the theoretical relationship between the functional and antigenic values for $\alpha_1$ PI and $\alpha_2$ M has been empirically derived allowing, for the first time, the calculation of their specific activities in serum. The serum concentration of $\alpha_1$PI was found to be highly correlated with residual uninhibited PPE catalytic activity in healthy individuals, but not in individuals exhibiting fragmented or complexed $\alpha_1$PI. Using these techniques, both the antigenic and functional levels of $\alpha_1$PI were determined in sera from subjects with insulin-dependent diabetes mellitus (IDDM) who has been clinically diagnosed as having either periodontal disease or gingival health. Determination of quantitative levels by antigen-capture suggests that the IDDM subjects with periodontitis manifest dramatically increased levels of fragmented serum $\alpha_1$PI compared with their orally healthy counterparts or normal controls.

The following abbreviations are employed in the specifications and amended claims:

PPE—porcine pancreatic elastase
$\alpha_1$PI—$\alpha_1$ proteinase inhibitor ($\alpha_1$-antitrypsin)
$\alpha_2$M—$\alpha_2$ Macroglobulin
HNE—human neutrophil elastase
I$\alpha$I—inter-$\alpha$-trypsin inhibitor
APE—porcine pancreatic elastase
PBS—0.01M phosphate, 0.15M NaCl, pH 7.2
TBS—0.05 M Tris, 0.15M NaCl, pH 7.8
Sa$_q$NA—succinyl-L-Ala-L-Ala-L Ala p-Nitro-anilide.
EDTA—ethylenediaminotetraacetic acid
ACD—acetate-citrate-dextrose
IDDM—insulin-dependent diabetes anellites

SUMMARY OF THE INVENTION

In its broad aspect, the present invention relates to a method for the quantitative determination of active and inactive proteinase inhibitors. The method comprises the steps of:

a) obtaining a sample of a body fluid from a subject;

b) preparing a first plurality of serial dilutions of the fluid of decreasing concentrations;

c) incubating the dilutions with varying concentrations of porcine pancreatic elastase and monitoring the catalytic activity which decreases linearly in relation to the dilutions of the fluid to a minimum point after which the catalytic activity increases linearly in relation to this dilution of the fluid;

d) by means of regression analysis calculating the coordinates of the intersection of two linear lines formed by the fluid concentration and residual activity; and e) calculating the functionally active proteinase inhibitor by computer-fit least squares regression analysis and comparing with a standard curve.

DESCRIPTION OF THE PREFERRED EMBODIMENTS

Figure 1A:
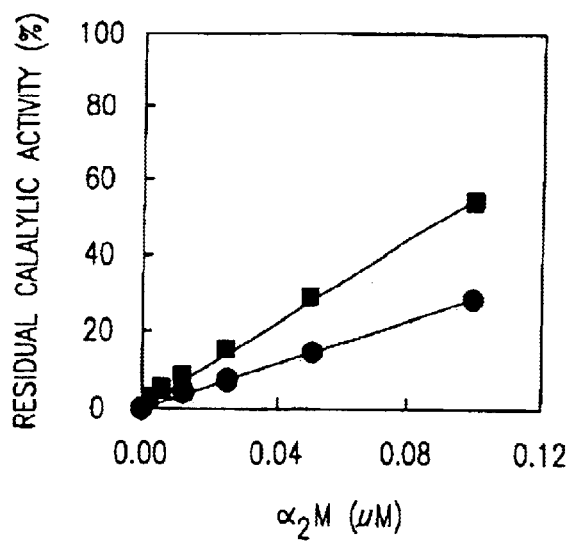
FIGS. 1A–1C depict competitive assays for $\alpha_1$PI (black squares) and $\alpha_2$M (black circles).

The stoichiometric relationship between $\alpha_2$M with any proteinase and interactive proteinase inhibitor can therefore be used to derive the precise equation to calculate the specific activity and inactive concentration of the active concentrations of the proteinase inhibitor in serum or other complex body fluids. The active concentrations of proteinase inhibitors can be determined by the present invention without interference by the presence of substrates, buffering pH, temperatures or optical detection device—the active concentration of proteinase inhibitors can be determined in blood corrected with no additive (serum), or into tubes containing the anticoagulants heparin, EDTA or ACD or any other anticoagulant.

The method of the present invention is effective for the determination of the active and inactive concentration of a proteinase inhibitor in complex body fluids using a wide variety of proteinases. For example, serine proteinases can be employed to quantitate serine proteinase inhibitors, aspartyl proteinases to quantitate aspartyl proteinase inhibitors, cystine proteinases to quantitate cystine proteinase inhibitors, metalloproteinase to quantitate metalloproteinase inhibitors, and the like.

The method is useful regardless of whether the proteinase is reversibly or irreversibly bound by the proteinase inhibitor of interest or whether the inhibitor is synthetic, transgenic or exogenously induced to expression. Also, the method is effective whether the proteinase inhibitor is bacterial, viral or parasitic or associated with a specific organ or cell type. The proteinase inhibitor can be introcellular, involved in coagulation, fibrinolysis, or complement inactivation and still be determinable by the present method.

As indicated, the present invention is directed to the quantitative determination of $\alpha_1$ proteinase inhibitors in bodily fluids. While the invention is of particular use in the determination of $\alpha_1$ proteinase inhibitors in human serum or plasm, it can also be used in determinations on any bodily fluid collected for clinical laboratory analysis including urine, saliva, seminal fluid, ascites, tears, nasal specimens, vaginal specimens and the like.

In practice, the method of this invention is a useful diagnostic tool for evaluating the medical condition in man and animals. Such condition can include but are not limited to, arthritis, atherosdersosis, diabetes, asthma, systemic lupus erythematosis; conditions which are of lymphoid origin, such or agammoglobulinemia, hypogarnmaglobulinemia, hypergammaglobulinemia, NK cells, T-lymphocytes, B-lymphocytes, thymocytes, bone marrow or null cells; conditions which are age-related illnesses, or anaphylatic; and conditions which involve a malignant illness, including but not limited to, lymphoma, leukemia, or tumors of any origin primary or secondary.

The condition can be autoimmune illness, or infection of bacterial, viral, or other parasitic origin. It can be a demyelinating disease or a degenerative disease of any tissue; or the condition can be genetic, hemolytic anemia, or cardiovascular; or related to a toxin or toxoid including cholera, pertussis, diphtheria, tetanus of E. coli.

The method of the present invention is also useful where the condition is related to a poison, such as stings, bites, ingested poisons, or those which contact the skin. The condition can be murosal including gastrointestinal disorders, pulmonary, a granulomatous, one that is inflammatory, an immune disorder, or an unknown condition. The condition can be one which is secondary to any pathologic process, such as those mentioned above.

The method can be used as a therapeutic tool for many medical conditions such as organ transplantation, transfusions, inducing immune tolerance, immunization, vaccination, inducing immune suppression or activations and for replacement therapy.

The following reagents were employed in the examples:

Porcine pancreatic elastase, type 1(EC 3.4.21.36, lot No. 16H8045, Sigma, St. Louis, Mo.) or human neutrophil elastase (EC 3.4.21.37, lot No. #EH9602a, Athens Research and Technology, Inc., Athens, Ga.) were active-site titrated in 0.05 M Tris, 0.15 M NaCl, pH 7.8, (TBS) using the substrate N-t-boc-L-alanine p-nitrophenyl ester (lot No. 46F-0330, Sigma), and the steady state was determined by optical absorbence at 410 nm in a Vmax kinetic microplate reader (Molecular Devices, Palo Alto, Calif.) for 3 min with 6-s intervals (30 measurements) at 20° C. The functionally active fractions of preparations of $\alpha_1$PI (Sigma A6150, lot No. 82H9323) and $\alpha_2$M (generous gift of Dr. Hanne Grø, Duke University Medical Center, Durham, N.C.) were determined. One mole of PPE was found to saturate 12.12 mol $\alpha_1$PI and 1.10 mol $\alpha_2$M, suggesting that $\alpha_1$PI and $\alpha_2$M were 8 and 91% active, respectively. Concentrations of HNE, PPE, $\alpha_1$PI, and $\alpha_2$M throughout represent the functionally active concentrations. Residual catalytic activity refers to uninhibited PPE in the presence of competing $\alpha_1$PI and $\alpha_2$M.

The following examples are illustrative of the invention:

EXAMPLE 1

Serum or Plasma Collection

Blood was collected with informed consent from healthy volunteers using Vacutainer tubes (Becton Dickinson, Rutherford, N.J.) Containing either heparin, ethylenediaminetetraacetic acid (EDTA, $K_3$), acetate-citrate-dextrose (ACD, Solution A), or no additive. Serum was prepared from blood collected in tubes with no additive by allowing blood to clot for 1 h at 2° C. and 2 h at 20° C. followed by centrifugation at 200 g for 10 min. Serum was stored at −70° C., thawed at 37° C., and maintained at 2° C. for no longer than 3 days before discarding. Two subjects, Nos. 2 and 6, were asked to participate based on known $\alpha_1$PI deficiency. Sera from patients with documented insulin-dependent diabetes mellitus (IDDM) were collected in the School of Dentistry during routine examination.

EXAMPLE 2

Quantitation of $\alpha_1$PI by ELISA

Wells of microtiter plate (Nunc, Denmark) were coated overnight at 20° C. with the immunoglobulin fraction of chicken anti-$\alpha_1$PI (lot No. 18823680, O.E.M. Concepts, Toms River, N.J.) at a concentration of 0.5 µg/ml in 0.02 M carbonate-bicarbonate buffer, pH 9.4. Microtiter plates were washed once in 0.01 M sodium phosphate buffer, 0.15 M NaCl, pH 7.2 (PBS), containing 0.05% Tween-20 (PBS-Tween) and blocked for 60 min at 20° C. with 5% fish gelatin (Norland, N. Brunswick, N.J.) in PBS-Tween. After washing once, wells were incubated for 60 min at 20° C. with serum serially diluted twofold beginning with a 1/1000 dilution in a 100-µl volume of 5% fish gelatin, PBS-Tween. After washing three times, wells were incubated for 60 min at 20° C. with polyclonal rabbit anti-human $\alpha_1$PI (lot No. 0180, Boehringer Mannheim, Indianapolis, Ind.) at a concentration of 1/4000 in 5% fish gelatin, PBS-Tween. After washing three times, wells were incubated for 60 min at 20° C. with horseradish peroxidase-coupled goat anti-rabbit immunoglobulin (lot No. 025H-4831, Sigma) at a concentration of 1/4000 in 5% fish gelatin, PBS-Tween. After being washed five times, the ELISA was developed using the substrate orthophenylenediamine HCl (0.4 mg/ml in 0.05 M citrate buffer, PH 5.0, containing 0.025% $H_2O_2$). The initial slopes were determined at 490 nm in a Vmax kinetic microplate reader (Molecular Devices) and concentrations from at least four sequential dilutions of a single serum sample were calculated based on standard curves of $\alpha_1$PI (1.6–200 nM). Standard deviations were less than 10% of the mean suggesting little interference in the ELISA from serum contaminants such as complement.

To detect the fraction of serum $\alpha_1$PI in complex with HNE, polyclonal rabbit anti-human neutrophil elastase (anti-HNE, lot No. 8K3185, Biodesign, Kennebunkport, Me.) at a concentration of 1.1000 in 5% fish gelatin, PBS-Tween, was used in the detection step. Quantitation was based on a standard curve of preformed equimolar complexes (1.6–200 pM) between $\alpha_1$PI and HNE (Athens Research & Technology).

EXAMPLE 3

Residual Catalytic Activity

It has been previously demonstrated that a serum dilution exists at which minimum catalytic activity can be measured by exploiting the properties of unequal serum concentration and unequal outcomes of proteinase complexes with $\alpha_1$PI and $\alpha_2$M. The maximum reduction in catalytic activity of elastase was used to determine the functionally active concentration of $\alpha_1$PI.

A PPE standard curve was prepared in each microtiter plate, and units of activity were determined where one unit is defined as the amount of PPE that hydrolyzes 1 $\mu$M of the elastase substrate, succinyl-L-Ala-L-Ala-L-Ala-p-nitroanilide ($SA_3NA$, Sigma), per minute at 20° C. at pH 7.8. Serum was serially diluted twofold in wells containing 50 $\mu$l TBS. Final serum concentrations for each sample ranged from 0.05 to 20%. PPE was added to wells in a 10-$\mu$l volume at an estimated concentration of 50 U and incubated for 2 min at 37° C. followed by 25 $\mu$l $SA_3NA$ in TBS with a final concentration of 0.6 mM in 0.06% dimethyl sulfoxide ($Me_2SO$). The maximum (100%) PPE activity was determined in each microtiter plate by incubating in TBS lacking serum. Optical absorbency ($\Delta mOD_{405}$/min) was monitored at 405 nm for 15 min with 6-s intervals (151 measurements) in a Vmax kinetic mincroplate reader (Molecular Devices) at 20 °C. Activity was calculated using the initial 30 measurements by regression analysis ($r^2>0.98$) and expressed as units of activity ($\mu$M/min) based on a final volume of 85 $\mu$l having a path length of 0.18 cm. Activity was determined for each of 8 or 16 different serum concentrations, and the serum concentration demonstrating the greatest reduction in activity was determined by regression analysis performed for these concentrations. The uninhibited PPE activity at this serum concentration is represented as a fraction of the total activity residual catalytic activity ($\mu$M) residual catalytic activity ($\mu$M)

$$\text{residual catalytic activity } (\mu M) = \frac{\text{uninhibited } PPE \text{ activity } (\mu M/\min)}{\text{maximum } PPE \text{ activity } (\mu M/\min)} \quad [1]$$

HNE was substituted for PPE in one set of measurements. For comparison, exogenous $\alpha_1$PI or $\alpha_2$M were added to sera prior to measuring activity.

The validity of determining the functional concentration of serum $\alpha_1$PI using residual catalytic activity was established by comparing the same measurements using purified preparations $\alpha_1$PI, $\alpha_2$M, PPE, and HNE. Catalytic activity for a constant concentration of active-site titrated PPE (0.2 $\mu$M) was measured after incubation with varied concentrations of functionally determined $\alpha_2$M (0.0008–0.1 $\mu$M) either before (Ganrot Assay) or after (competition assay) addition of excess functionally determined $\alpha_1$PI (1 $\mu$M). In these experiments, the theoretical fraction of PPE bound to each concentration of $\alpha_2$M was calculated assuming 1:1 stoichiometry as theoretical molecules PPE/molecule $\alpha_2$M $$= \frac{\alpha_2 M (\mu M)}{PPE\ (0.2\ \mu M)}, \quad [2]$$

where $\alpha_2$M and PPE represent the active concentrations. The fraction of PPE actually bound to $\alpha_2$M was empirically determined in the presence of various concentrations of $\alpha_2$M and excess $\alpha_1$PI, and this value was calculated as molecules PPE/molecule $\alpha_2$M $$= \frac{\text{residual catalytic activity}}{\text{theoretical molecules } PPE/\text{molecule } \alpha_2 M} \quad [3]$$

The fraction of PPE bound to $\alpha_1$PI was calculated from the competition assay as molecules PPE/molecule $\alpha_1$PI $$=1-\text{molecules PPE/molecule } \alpha_2 M. \quad [4]$$

Western Blot Analysis

Electrophoresis on 0.75-mm gels composed of 12% total polyacrylamide was performed using standard SDS-polyacrylamide gel electrophoresis buffers in reducing conditions after boiling samples 5 min, Proteins were transferred to Immobilon (Millipore Corp., Bedford, Mass.) by electrophoresis of proteins in 0.025 M Tris, 0.193 M glycine, 20% MeOH, and blocked in 3% nonfat, dried milk. For detection of $\alpha_1$PI, blots were incubated with rabbit anti-$\alpha_1$PI (0.7 $\mu$g/ml, Boehringer Mannheim). Binding was detected by incubation of blots with horseradish peroxidase conjugated with goat anti-rabbit immunoglobulin (1/1000, Sigma). After being washed extensively, substrate consisting of 0.3 mg/ml 3,3'-diaminobenzidine in 20 mM Tris, pH 7.4, 0.3 M NaCl, 0.03% $H_2O_2$ was added.

EXAMPLE 4

Determination of $\alpha_1$PI Antigen Concentration in Serum

A sandwich ELISA was developed for quantitating $\alpha_1$PI in serum, as well as the proportion $\alpha_1$PI complexed with HNE. Incubation of untreated serum or plasma with immobilized antibodies in a microtiter plate can initiate complement activation and aggregation of proteins resulting in unreliable values. Because chicken antibodies have been shown to lack the capacity to activate human complement, serum $\alpha_1$PI was first captured with chicken anti-human $\alpha_1$PI. It was observed that sensitivity and consistency were improved when values were based on estimates of Vmax as opposed to the traditional endpoint method (data not shown). Since gender differences in $\alpha_1$PI quantitative levels have been reported, healthy adult males and healthy adult females were recruited for the study (Table 1) below. Siblings having known $\alpha_1$PI deficiency were recruited for the study. Genotype analysis by PCR was performed by Dr. R. Farber, UNC Hospitals, to confirm that these individuals were homozygous for the deficient $Pi_{zz}$ allele. Because serum concentrations of $\alpha_1$PI are routinely measured using nephelometric methods, the antigenically quantitated level a $\alpha_1$PI in serum from Subject No. 6 was confirmed by nephelometry (Dr. J. Katzmann, Mayo Clinic, Rochester, Minn.). Serum concentrations of $\alpha_1$PI were found to be 3.27+/=1.3 μM by the ELISA method and 4.18 μM by nephelometry. By ELISA, healthy individuals demonstrated a wide range of serum levels of $\alpha_1$PI (10–84 μM) with a minor fraction (0.3–0.4%) in complex with HNE. The individuals with known $\alpha_1$PI deficiency demonstrated roughly 10% normal $\alpha_1$PI levels (3–5 μM) and a proportionally increased fraction (3%) was HNE complexed.

Determination of Functional $\alpha_1$ 1PI and $\alpha_2$M in Serum

Hypothetically, the difference in the residual uninhibited catalytic activity in the Ganrot assay and the residual activity in the competitive assay represents the concentration of competing $\alpha_1$PI as long as all other contaminating proteins (e.g., IaI) are without influence. To establish the validity for measuring elastase inhibitory capacity of $\alpha_1$PI in the presence of competing $\alpha_2$M, the molecular ratios at which $\alpha_1$PI and $\alpha_2$M demonstrate competitively equivalent elastase binding capacity were examined using isolated proteins. PPE was incubated with a constant concentration of $\alpha_1$PI in the presence of varying concentrations of competing $\alpha_2$M (competition assay). These values were compared with those obtained using the Ganrot assay in which PPE was incubated with varying concentrations of $\alpha_2$M and subsequently incu-

TABLE 1

Functional Concentrations of Serum $a_1$PI and $a_2$M in an Asymptomatic Normal Population

| Subject | Sex | Age | $a_1$PI (μM)[a] | $a_1$PI in Complex With HNE (μM)[b] | Residual PPE (μM)[d] | Serum Concentration[d] | Active $a_1$ PI (μM)[e] | Active $a_2$M (μM)[f] |
|---|---|---|---|---|---|---|---|---|
| 1 | M | 22 | 36.5 = 1.9 | 0.12 | 0.1590 | 0.0090 | 39.45 | 5.57 |
| 2 | M | 47 | 4.8 = 0.8 | 0.14 | 0.5433 | 0.0429 | 3.39 | 2.04 |
| 3 | M | 45 | 22.0 = 3.8 | 0.09 | 0.2129 | 0.0138 | 22.02 | 6.57 |
| 4 | M | 45 | 32.6 = 5.1 | n.d. | 0.2190 | 0.0083 | 20.82 | 4.93 |
| 5 | M | 27 | 37.6 = 5.0 | n.d. | 0.1403 | 0.0085 | 50.66 | 8.86 |
| 6 | F | 43 | 3.3 = 1.3 | 0.12 | 0.6390 | 0.0553 | 2.45 | 1.79 |
| 7 | F | 39 | 10.0 = 1.5 | 0.07 | 0.3264 | 0.0132 | 9.37 | 2.65 |
| 8[c] | F | 44 | 3.5 = 1.1 | n.d. | 0.5319 | 0.0131 | 3.53 | 1.70 |
| 9 | F | 43 | 26.0 = 2.5 | n.d. | 0.2128 | 0.0032 | 22.03 | 8.81 |
| 10 | F | 44 | 84.4 = 13.4 | n.d. | 0.1152 | 0.0061 | 75.12 | 4.28 |
| 11 | F | 37 | 40.1 = 5.0 | 0.14 | 0.2697 | 0.0034 | 13.72 | 3.50 |
| 12 | F | 45 | 45.5 = 2.5 | n.d. | 0.1656 | 0.0060 | 36.39 | 4.65 |
| 13 | F | 31 | 29.9 = 2.6 | n.d. | 0.1978 | 0.0074 | 25.52 | 1.94 |
| 14 | F | 49 | 37.0 = 12.1 | n.d. | 0.1573 | 0.0073 | 40.34 | 2.20 |
| 15[h] | M | 41 | 282.8 = 42.1 | n.d. | 0.2240 | 0.0019 | 19.89 | 6.35 |

Figure 3:
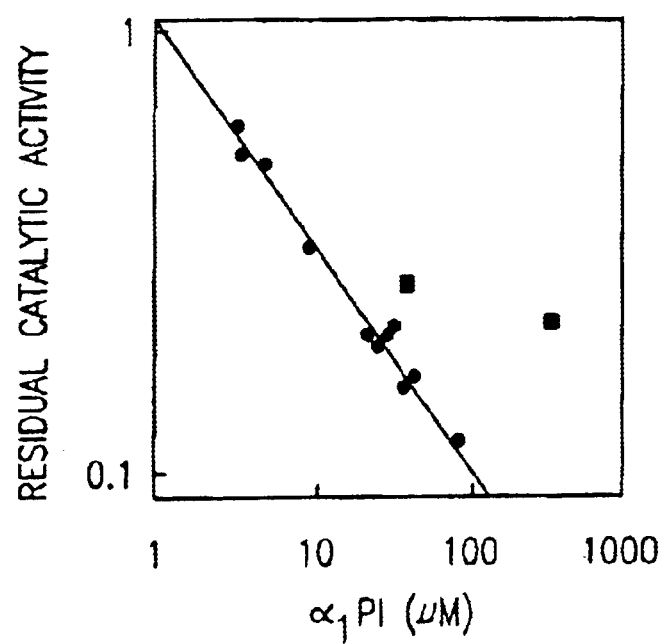
FIG. 3 depicts the relationship between residual catalytic activity and antigenically quantitated levels of $\alpha_1$PI.

[a]Mean = standard deviation measured in ELISA by capturing with anti-$\alpha_1$ PI and detecting with anti-$a_1$ PI.
[b]Measured in ELISA by capturing with anti $\alpha_1$ PI and detecting with anti-HNE.
[c]Not done.
[d]Measured as described in FIG. 2.
[e]Measured as described in FIG. 3 using Eq. (6).
[f]Measured as described in FIG. 4 using Eq. (7).
[g]Sample collected from Subject No. 6 at a different time point.
[h]This IDDM periodontally diseased subject is included to demonstrate the discrepancy between $a_1$ PI quantitations by graphical representation in FIG. 4.

EXAMPLE 5

Determination of Residual Catalytic Activity

Figure 1B:
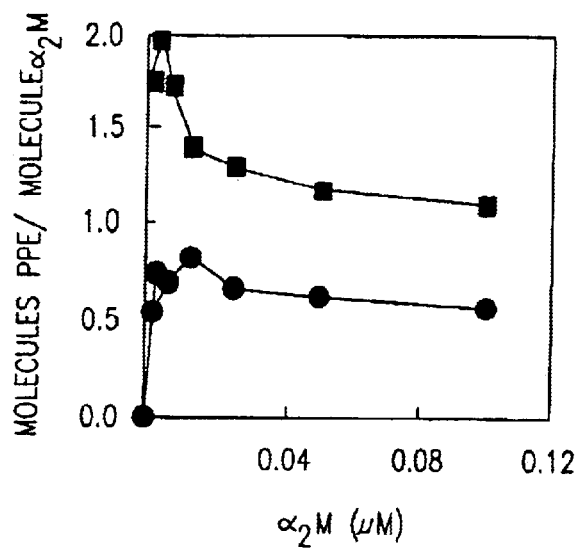
Figure 1C:
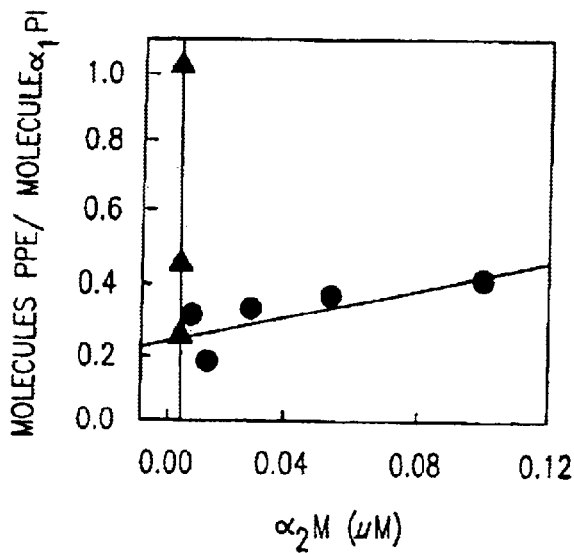
Figure 2A:
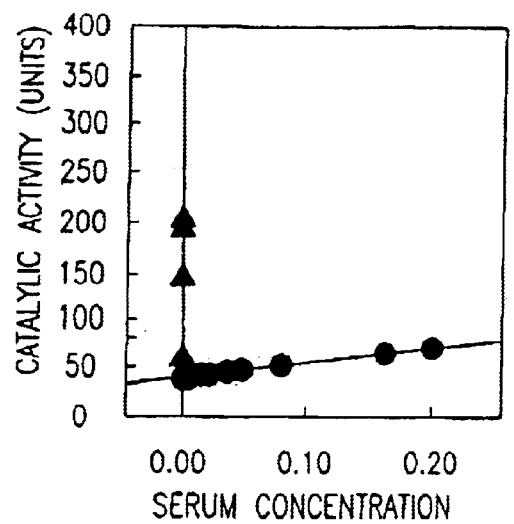
FIGS. 2A–2F show serum concentration vs. catalytic activity from which residual catalytic activity is calculated.
Figure 2B:
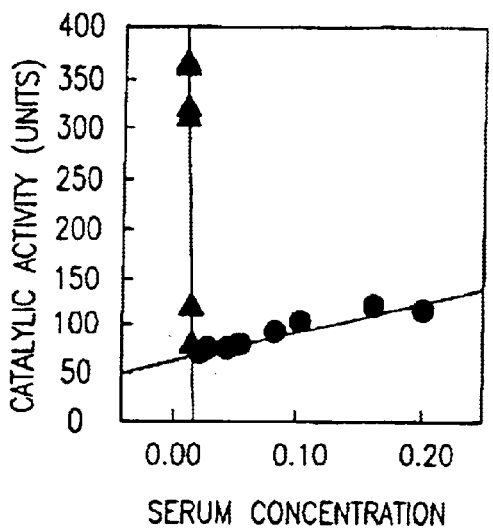
Figure 2C:
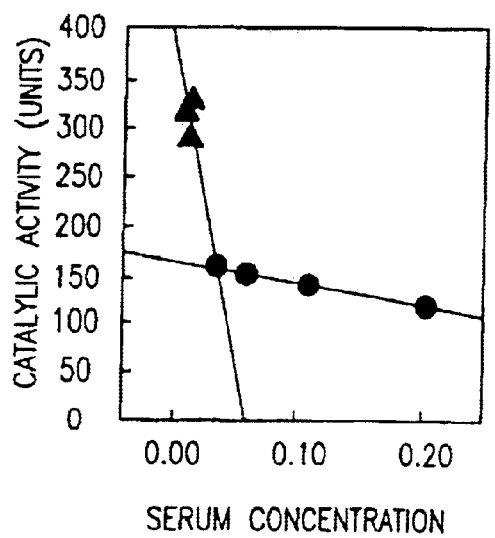
Figure 2D:
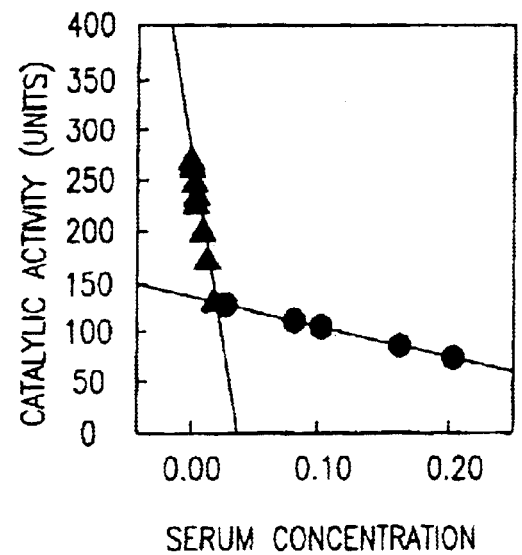
Figure 2E:
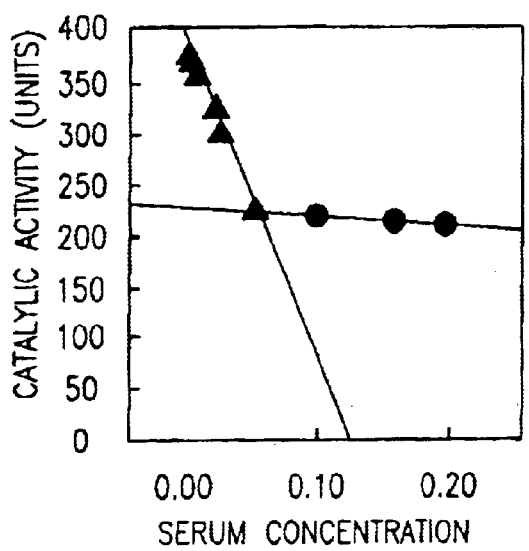
Figure 2F:
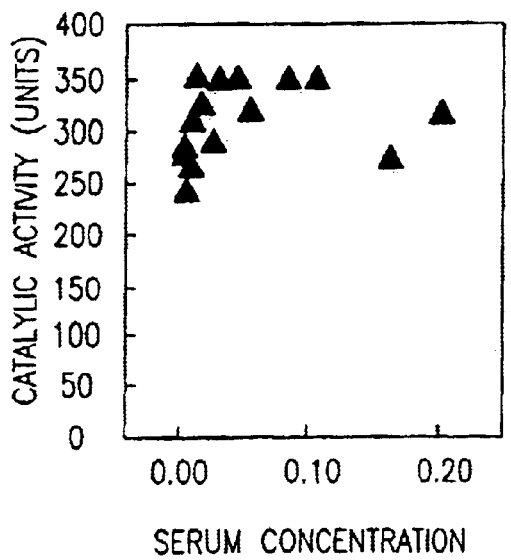

The covalent nature of the interaction of PPE within $\alpha_2$M has been shown to be at a site not inhibitory for the catalytic site of PPE, and this property allows $\alpha_2$M-complexed PPE to retain discretionary cleavage of low-molecular-weight substrates such as $SA_3NA$. In contrast, incubation of PPE with $\alpha_1$PI results in stoichiometrically decreased PPE activity. The rate of association of PPE to $\alpha_2$M ($4.4 \times 10^6$ $M^{-1}$ $s^{-1}$) is 44-fold greater than that of PPE to $\alpha_1$PI ($1 \times 10^5$ M–1 $s^{-1}$), and this suggests that in the presence of sufficient competing concentrations of $\alpha_2$M, PPE should not be inhibited by $\alpha_1$PI. This principle forms the basis for the Ganrot Assay which allows determination of $\alpha_2$M activity by first saturating $\alpha_2$M in the presence of a 2:1 molar excess of PPE: $\alpha_2$M after which the noncomplexed proteinase is neutralized by incubation with 10:1 molar excess $\alpha_1$PI:$\alpha_2$M. The stoichiometry of PPE binding to $\alpha_1$PI is 1:1. Although each molecule of $\alpha_2$M has the capacity to bind two proteinase molecules, it has been mechanistically documented that excessively great proteinase concentrations are necessary to achieve a 2:1 stoichiometry.

bated with a constant concentration of $\alpha_1$PI. As expected, residual uninhibited catalytic activity was diminished in the competition assay in comparison to activity using the Ganrot assay (FIG. 1A). In the Ganrot assay, a 2:1 ratio of PPE (0.2 μM) to $\alpha_2$M (0.1 μM) resulted in 1.1 molecules PPE bound to 1 molecule $\alpha_2$M (FIG. 1B), and this result is consistent with previous mechanistic studies demonstrating binary $\alpha_2$M:proteinase complexes. As the ratio of $\alpha_2$M to PPE approached 60:1, two molecules of PPE were associated with one molecule $\alpha_2$M. In contrast, in the competition assay, fewer than 0.6 molecules of PPE were associated with one molecule $\alpha_2$M as the ration of PPE to $\alpha_2$M approached 60:1. The protection of PPE by $\alpha_2$M in the competition assay was relatively constant when the ration of $\alpha_2$M (0.0031–0.1 μM) to $\alpha_1$PI (1 μM) was between 1:100 and 1:320 (FIG. 1C). When the concentration of $\alpha_2$M fell below these values, the protection of PPE by $\alpha_2$M decreased in proportion. At the intersection of the two regression lines, the concentrations of PPE, $\alpha_2$M, and $\alpha_1$PI are 0.31, 0.003, and 1.0 μM, respectively.

Reliability of Residual Catalytic Activity as a Measure of Serum $\alpha_1$PI Serum dilutions were incubated with varying concentrations of PPE, and catalytic activity was monitored (FIGS.

2–2F). Catalytic activity was found to decrease linearly in relation to the dilution of serum to a minimum point, after which the catalytic activity increased linearly in relation to the dilution of serum. Regression analysis was used to calculate the coordinates of the intersection of these two lines, the maximum reduction in catalytic activity. As expected, the abscissa (serum concentration) and ordinate (residual catalytic activity) at the intersection were found to increase in collinear manner in the presence of increasing PPE. In other words, increased serum concentration (and $\alpha_1$PI concentration) was necessary to achieve maximum inhibition using increased PPE; likewise, increased PPE resulted in increased residual PPE activity at the point of maximum inhibition. Since a collinear relation exists between the concentration of PPE and the values of the coordinates at the intersection, residual catalytic activity at the serum dilution demonstrating maximum inhibition can be reliably estimated as the fraction of total PPE activity (0.2008+/=0.0138 for Subject No. 11). Variation in multiple determinations of residual catalytic activity for a single serum sample was <1% using consistent concentrations of active-site titrated PPE (near 50 U). Values for some subjects in this study were calculated using sera collected on more than one occasion, and variation in residual catalytic activity observed to occur between different sera collections (1–13%) was interpreted as true variations in residual catalytic activity.

As expected, when exogenous $\alpha_1$PI (2.7 μM) was added to serum, residual catalytic activity decreased representing an increased concentration of $\alpha_1$PI. When exogenous $\alpha_2$M (2.7 μM) was added to serum, residual catalytic activity increased representing increased protection of PPE. In this experiment, the concentration of $\alpha_2$M was added in great excess to demonstrate its effect on the distribution of PPE activity. Since the physiologic concentration of $\alpha_2$M is 1.56–4.96 μM, and proteinase-complexed $\alpha_2$M is rapidly cleared (half-life 2–4 min), fluctuations in serum concentrations of $\alpha_2$M would not be expected to significantly affect measurements of serum $\alpha_1$PI Results suggest that approximately 50% of the exogenous $\alpha_1$PI (1.50+/=0.44, μM) and 80% the exogenous $\alpha_2$M (2.23+/=0.45 μM) were inactivated upon addition probably as a result of proteolysis. However, these results support the hypothesis that residual PPE catalytic activity is primarily determined by the functionally active fractions of $\alpha_1$PI and $\alpha_2$M.

Comparison of Residual Catalytic Activity in Serum and Plasma

Evidence has suggested that heparin decreases the rate of $\alpha_1$PI inhibition of HNE, but not PPE. The residual catalytic activities were compared in a single individual when blood was collected with no additive (serum) or into tubes containing the anticoagulants heparin, EDTA or ACD. The residual catalytic activity for plasma collected in ACD (0.276) was greater than that for plasma collected in heparin or EDTA or for serum (0.2373=/+0.0018). These results suggest that serum or plasma can yield equivalent residual catalytic activities using this method.

Serum from a patient (No. 15) previously determined to have a history of infection with periodontopathogenic bacteria exhibited higher than normal quantitative levels (283 μM), but low normal functional levels of $\alpha_1$PI (20 μM). When serum from this patient was examined by Western blot, proteolytic fragmentation was observed. Serum from Subject No. 11 also exhibited evidence of fragmentation compared with that of Subject Nos. 6 and 13. These results suggest that increased antigenic levels of $\alpha_1$PI as determined by ELISA or nephelometry might not be representative of the functionally active $\alpha_1$PI.

Determination of the Relationship Between Residual Catalytic Activity and the Functional Concentrations of Serum αPI and $\alpha_2$M It was found that residual catalytic activity decreased in direct relation to increased $\alpha_1$PI concentration in healthy individuals (FIG. 3). Based on these individuals, the relationship between residual catalytic activity and functionally active $\alpha_1$PI was determined using computer-fit least-squares regression analysis to be:

$$\log(x) = \frac{\log(y)}{-0.5}$$

where x represents the functional concentration of $\alpha_1$PI (μM), and y represents residual catalytic activity of PPE (μM). This equation is equivalent to:

$$\text{Log}[\alpha_1 PI] = \frac{\log(PPE)}{\log(0.316)} \quad [6]$$

which corresponds to a ratio of PPE:$\alpha_1$PI equivalent to 0.316:1. This ration is virtually identical to the ratios for PPE:$\alpha_2$M:$\alpha_1$PI determined using isolated proteins in FIG. 1 which were 0.31:0.003:1.0.

The stoichiometric relationship between PPE, $\alpha_1$PI AND $\alpha_2$M demonstrated in FIG. 1 suggests that $\alpha_2$M might also be estimated using concentrations of PPE and $\alpha_1$PI. Since two molecules of PPE were shown to associate with $\alpha_2$M when the concentration of PPE exceeded 60-fold $\alpha_2$M, the serum concentration of $\alpha_2$M was estimated using the serum concentrations at which PPE and $\alpha_2$M have 1:1 stoichiometry as log[$\alpha_2$M]

$$\text{LOG}(A2m) = \frac{\log(\text{uninhibited } PPE \text{ activity}/\text{maximum } PPE \text{ activity})}{\log[\text{serum concentration}]} \quad [7]$$

The results of FIG. 1 suggest the concentration of $\alpha_2$M might also be calculated using $\alpha_1$PI using the ratio 0.003:1.0 (or 1:333) as $$\text{Log}[\alpha_2 M] = \frac{\log[\alpha_1 PI]}{\log[333]}$$

Based on Eqs. [7] and [8], the average $\alpha_2$M concentration of these individuals was 3.32+/=1.27 μM and 3.25+/=1.20 μM, respectively, and these values are within the previously reported range, 1.56–4.96 μM determined by antigen capture. However, because $\alpha_2$M has broad specificity, proteinases that do not compete for and are not eliminated by a $\alpha_1$PI retain their capacity to interact with and diminish $\alpha_2$M, and this effect escapes detection by the methods described here. This suggests that measuring $\alpha_2$M by competition with $\alpha_1$PI might vary as a result of serum proteinases other than elastase. Further examination of the behavior of $\alpha_2$M by comparison using ELIS or the Ganrot assay is needed for verification of the measurements described here.

Comparison of HNE with PPE as a Measure of Serum of $\alpha_1$PI

Figure 4A:
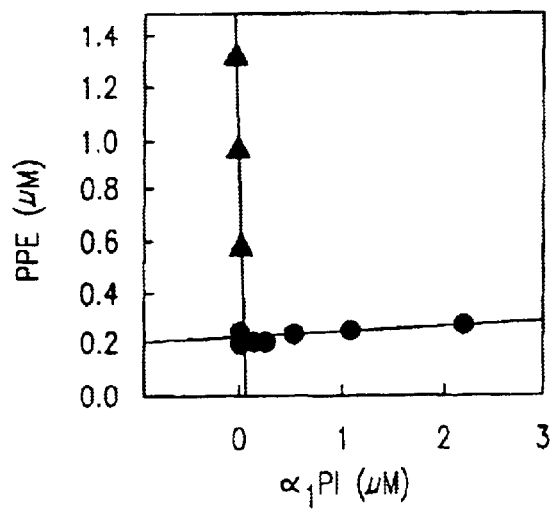
FIGS. 4A–4C shows a comparison of HNE and PPE in measuring serum $\alpha_1$PI.
Figure 4B:
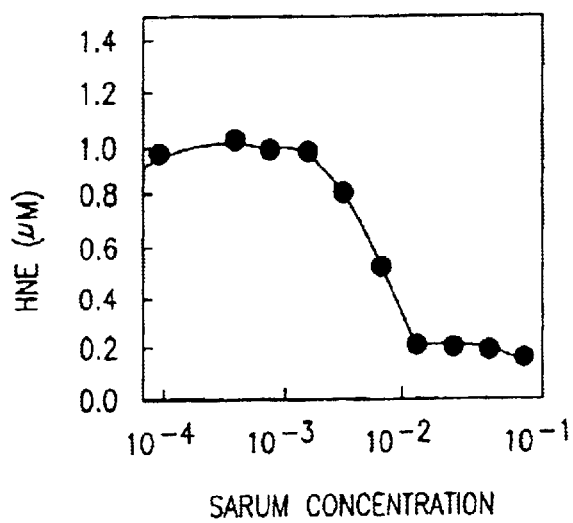
Figure 4C:
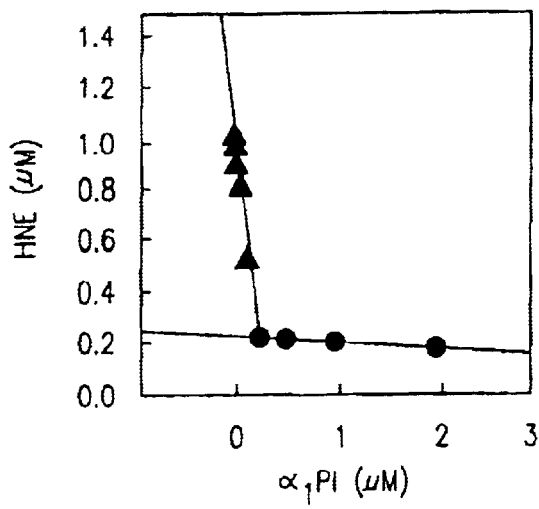

Although $\alpha_2$M inhibition of proteinases including PPE involves covalent proteinase interaction with a thiol ester, the noncovalent complex between HNE and $\alpha_2$M has been shown to be unique in lacking a thiol ester bond. The rate of association of HNE for $\alpha_1$PI ($6.5\times10^7$ $M^{-1}s^{-1}$). During the acute phase, $\alpha_1$PI increases 2- to 4-fold, and this is consistent with the critical ratio for $\alpha_1$PI:$\alpha_2$M during control of HNE. In the absence of influence by other serum inhibitors, measurement of residual catalytic activity with HNE or PPE should yield identical values for $\alpha_1$PI concentration. Residual catalytic activity of a single serum sample was compared using PPE or HNE as described. Based on the relationship described in FIG. 3, total $\alpha_1$PI concentration was determined to be 22.25 $\mu$M. To more easily compare molar relationships, serum concentrations were converted to represent $\alpha_1$PI concentrations (FIG. 4A). In parallel, residual catalytic activity of the same serum sample was measured using HNE. As expected, HNE was found to exhibit bimodal activity when varying concentrations of serum were incubated with a constant concentration of active-site titrated HNE (FIG. 4B). Based on total serum $\alpha_1$PI as determined using PPE (22.25 $\mu$M), the serum concentrations between $10^{-1}$ and $10^{-3}$ were converted to represent a1P concentrations (FIG. 4C). At the serum concentration (0.0107) displaying minimum catalytic activity, the HNE concentration was 0.2227 $\mu$M and the $\alpha_1$PI concentration was 0.2388 $\mu$M a ratio of 0.93:1. Then the total concentration of $\alpha_1$PI can be calculated from the serum concentration as $$\frac{0.238\ \mu M\ \alpha_1 PI}{0.0107} = 22.24\ \mu M$$

Since this value is virtually identical with the concentration of $\alpha_1$PI determined using PPE, it can be concluded that the assay is highly specific and that the empirically derived relationship accurately represents the theoretical relationship. Further, the consistency in these measurements suggests that serum inhibitors other than $\alpha_1$PI and $\alpha_2$M do not contribute significantly to inhibition of PPE or HNE.

Determination of Quantitative and Functional Levels of Serum $\alpha_1$PI in an IDDM Population It has been previously reported that patients with insulin-dependent diabetes mellitus have greater or lower (36–38) $\alpha_1$PI values compared with the normal population. Applying the methods developed here, the $\alpha_1$PI quantity and function in a population of IDDM patients with and without periodontal disease were determined. Because IDDM patients are known to have altered glaciation of secreted proteins, patients demonstrating aberrant glycosylated hemoglobin were eliminated from the study. The results clearly demonstrate that there is a significant quantitative difference between the IDDM and the normal population. However, when IDDM patients are dichotomized based on evidence of periodontal disease, it becomes apparent that IDDM patients without periodontal disease have normal levels of $\alpha_1$PI, whereas those with periodontal disease have significantly greater than normal $\alpha_1$PI. In comparison, when the elastase inhibitory capacity in these patients was determined, there was a less dramatic, although statistically significant, difference between subjects suggesting an underlying pathology perhaps of bacterial origin unrelated to periodontitis. These data suggest that although the IDDM patients manifesting periodontal disease have increased levels of antigenically determined a $\alpha_1$PI, a significant proportion maybe inactivated. Further, these data demonstrate an attendant systemic manifestation associated with periodontal disease in IDDM patients.

It is evident from the foregoing that the present inventions provides a reproducible, inexpensive and expedient method for determinations of the functionally active and inactive concentrations of $\alpha_1$PI and $\alpha_2$M in body fluids and in particular, in serum or plasma.

Although the invention has been illustrated by the preceding disclosures, it is not to be considered as being limited to the examples disclosed therein, but rather, the invention is directed to the generic area or hereinbefore disclosed. Various modifications and embodiments thereof may be made without departing from the spirit and scope thereof.

What is claimed is:

1. A method for a quantitative determination of active and inactive proteinase inhibitors in a bodily fluid which comprises the steps of:
   a. obtaining a sample of a bodily fluid from a subject;
   b. preparing a first plurality of serial dilutions of the fluid of decreasing concentration;
   c. incubating the dilutions with varying concentrations porcine pancreatic elastase (PPE) and monitoring the catalytic activity which decreases linearly in relation to the dilutions of the fluid to a minimum point, after which the catalytic activity increases in relation to the dilution of the fluid;
   d. by means of regression analysis calculating the coordinates of the intersection of two linear lines, one of which is formed by the fluid concentration and the other by residual catalytic activity; and
   e. calculating the active and inactive proteinase inhibitor activity by computer-fit least squares regression analysis and comparing with a standard curve.

2. The method of claim 1 wherein the proteinase inhibitor is $\alpha_1$PI.

3. The method of claim 1 wherein the proteinase inhibitor is $\alpha_2$M.

4. The method of claim 1 wherein the subject is human.

5. The method of claim 1 wherein the subject is animal.

6. The method of claim 1 wherein the bodily fluid is selected from the group consisting of blood serum, blood plasma, urine, saliva, seminal fluid, ascites, tears, nasal specimens, and vaginal specimens.

7. The method of claim 1 wherein the fluid is blood serum.

8. The method of claim 1 wherein the fluid is blood plasma.

9. A method for an evaluation of non-inflammation condition in a subject which comprises determining the quantity of active and inactive proteinase inhibitor in the subject by the method of claim 1.

10. The method of claim 9 wherein the condition is insulin—dependent diabetes mellitus.

* * * * *